United States Patent [19]

Hauser et al.

[11] Patent Number: 5,776,468
[45] Date of Patent: Jul. 7, 1998

[54] VACCINE COMPOSITIONS CONTAINING 3-0 DEACYLATED MONOPHOSPHORYL LIPID A

[75] Inventors: Pierre Hauser, Chaumont-Gistoux; Pierre Voet, Izel; Moncef Slaoui, Rixensart; Nathalie Marie-Josephe Claude Garcon-Johnson, Wavre; Pierre Desmons, Nivelles, all of Belgium

[73] Assignee: SmithKline Beecham Biologicals (S.A.), Rixensart, Belgium

[21] Appl. No.: 525,638

[22] PCT Filed: Mar. 14, 1994

[86] PCT No.: PCT/EP94/00818

§ 371 Date: Feb. 12, 1996

§ 102(e) Date: Feb. 12, 1996

[87] PCT Pub. No.: WO94/21292

PCT Pub. Date: Sep. 29, 1994

[30] Foreign Application Priority Data

Mar. 23, 1993 [GB] United Kingdom ............ 9306029
Feb. 23, 1994 [GB] United Kingdom ............ 9403417

[51] Int. Cl.$^6$ .................. A61K 39/29; A61K 39/39
[52] U.S. Cl. .................. 424/226.1; 424/192.1; 424/202.1; 424/282.1
[58] Field of Search ............ 424/184.1, 208.1, 424/226.1, 227.1, 231.1, 236.1, 278.1, 283.1, 192.1, 202.1, 282.1

[56] References Cited

U.S. PATENT DOCUMENTS

| 4,196,192 | 4/1980 | Kuo | 424/92 |
|---|---|---|---|
| 4,806,352 | 2/1989 | Cantrell | 424/92 |
| 4,857,634 | 8/1989 | Minor et al. | 530/324 |
| 4,877,611 | 10/1989 | Cantrell | 424/88 |
| 4,912,094 | 3/1990 | Myers et al. | |
| 5,026,557 | 6/1991 | Estis et al. | 424/450 |
| 5,100,662 | 3/1992 | Bolcsak et al. | 424/88 |

FOREIGN PATENT DOCUMENTS

| 339 667 | 11/1989 | European Pat. Off. |
| 0 414 374 | 2/1991 | European Pat. Off. |
| WO86/01826 | 3/1986 | WIPO |
| WO 92/06113 | 4/1992 | WIPO |
| WO92/06113 | 4/1992 | WIPO |
| WO92/11291 | 7/1992 | WIPO |
| WO 92/16231 | 10/1992 | WIPO |
| WO92/16231 | 10/1992 | WIPO |
| WO92/16556 | 10/1992 | WIPO |
| WO93/19780 | 10/1993 | WIPO |

OTHER PUBLICATIONS

Azuma, "Synthetic Immunoadjuvants: application to non-specific host stimulation and potentiation of vaccine immunogenicity", Vaccine 10, 1000–1006 (1992).

Andre et al., "Inactivated Candidate Vaccines for Hepatitis A", Prog. Med. Virol. 37, 72–95 (1990).

Szoka et al., "Comparative Properties and Methods of Preparation of Lipid Vesicles (Liposomes)", Ann. Rev. Biophys. Bioeng. 9, 467–508 (1980).

Coursaget et al., "Simultaneous Administration of Diphtheria-Tetanus-Pertussis-Polio and Hepatitis B Vaccines in a Simplified Immunization Program", Infection and Immunity, 51(3), pp. 784–787 (1986).

Primary Examiner—Marian C. Knode
Assistant Examiner—Donna C. Wortman

[57] ABSTRACT

Novel vaccine compositions comprising small particles of 3-O-deacylated monophosphoryl lipid A are provided. In particular the particle size is below 120 nm. Such vaccine compositions have superior immunological properties.

53 Claims, 1 Drawing Sheet

Fig. 1

VACCINE COMPOSITIONS CONTAINING 3-0 DEACYLATED MONOPHOSPHORYL LIPID A

This application is a 371 of PCT/EP94/00818 filed Mar. 14, 1994.

The present invention relates to novel vaccine formulations, methods for preparing them and to their use in therapy.

3-O-deacylated monophosphoryl lipid A (or 3 De-O-acylated monophosphoryl lipid A) has formerly been termed 3D-MPL or d3-MPL to indicate that position 3 of the reducing end glucosamine is de-O-acylated. For preparation, see GB 2 220 211 A. Chemically it is a mixture of 3-deacylated monophosphoryl lipid A with 4, 5 or 6 acylated chains. Herein the term 3D-MPL (or d3-MPL) is abbreviated to MPL since 'MPL' is a Registered Trademark of Ribi Immunochem., Montana which is used by Ribi to denote unambiguously their 3-O-deacylated monophosphoryl lipid A product.

GB 2 220 211A mentions that the endotoxicity of the previously used enterobacterial lipopolysacharides (LPS) is reduced while the immunogenic properties are conserved. However GB 2 220 211 cited these findings merely in connection with bacterial (Gram negative) systems. No mention of the particle size of the MPL was made. In fact the particle size of the known 3-O-deacylated monophosphoryl lipid A has particles in excess of 500 nm.

In WO 92/16231 a vaccine formulation comprising a Herpes Simplex Virus glycoprotein gD or immunological fragments thereof in conjunction with 3 deacylated monophosphoryl lipid A was disclosed. Again, no mention of the particle size of the 3 deacylated monophosphoryl lipid A was made.

In WO 92/06113 a vaccine formulation comprising HIV gp 160 or a derivative thereof such as gp 120 in conjunction with 3 deacylated monophosphoryl lipid A was disclosed. No mention of particle size of the MPL was made.

The present invention provides a vaccine composition comprising an antigen in conjunction with 3-O-deacylated monophosphoryl lipid A (abbreviated herein to MPL) and a suitable carrier wherein the particle size of the MPL is 'small' and in general does not exceed 120 nm when prepared.

Such a formulation is suitable for a broad range of monovalent or polyvalent vaccines.

Surprisingly, it has been found that vaccine compositions according to the invention have particularly advantageous properties as described herein. In particular such formulations are highly immunogenic. Additionally sterility of the adjuvant formulation can be assured as the product is susceptible to sterile filtration. A further advantage of 'small' MPL arises when formulated with aluminium hydroxide, as the MPL interacts with the aluminium hydroxide and the antigen to form a single entity.

In an embodiment of the invention, the antigen is a viral antigen, for example an antigen against hepatitis infection (Hepatitis A, B, C, D, or E) or herpes (HSV-1 or HSV-2) infection as described hereinbelow. A review on modern hepatitis vaccines, including a number of key references, may be found in the Lancet, May 12th 1990 at page 1142 ff (Prof A. L. W. F. Eddleston). See also 'Viral Hepatitis and Liver Disease' (Vyas, B. N., Dienstag, J. L., and Hoofnagle, J. H., eds. Grune and Stratton, Inc. (1984) and 'Viral Hepatitis and Liver Disease' (Proceedings of the 1990 International Symposium, eds F. B. Hollinger, S. M. Lemon and H. Margolis, published by Williams and Wilkins). References to HSV-1 and HSV-2 may be found in WO 92/16231.

Infection with hepatitis A virus (HAV) is a widespread problem but vaccines which can be used for mass immunisation are available, for example the product 'Havrix' (SmithKline Beecham Biologicals) which is a killed attenuated vaccine obtained from the HM-175 strain of HAV [see 'Inactivated Candidate Vaccines for Hepatitis A' by F. E. Andre, A Hepburn and E. D. Hondt, Prog Med. Virol. Vol 37, pages 72–95 (1990) and the product monograph 'Havrix' published by SmithKline Beecham Biologicals (1991)].

Flehmig et al (loc cit., pages 56–71) have reviewed the clinical aspects, virology, immunology and epidemiology of Hepatitis A and discussed approaches to the development of vaccines against this common viral infection.

As used herein the expression 'HAV antigen' refers to any antigen capable of stimulating neutralising antibody to HAV in humans. The HAV antigen may comprise live attenuated virus particles or inactivated attenuated virus particles or may be, for example an HAV capsid or HAV viral protein, which may conveniently be obtained by recombinant DNA technology.

Infection with hepatitis B virus (HBV) is a widespread problem but vaccines which can be used for mass immunisation are now available, for example the product 'Engerix-B' (SmithKline Beecham plc) which is obtained by genetic engineering techniques.

The preparation of Hepatitis B surface antigen (HBsAg) is well documented. See, for example, Harford et al in Develop. Biol. Standard 54, page 125 (1983), Gregg et al in Biotechnology, 5, page 479 (1987), EP-A-0 226 846, EP-A-0 299 108 and references therein.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et al, Nature, 317, 489 (1985) and references therein) HBsAg as herein described may, if desired, contain all or part of a pre-S sequence as described in the above references and in EP-A-0 278 940. In particular the HBsAg may comprise a polypeptide comprising an amino acid sequence comprising residues 12–52 followed by residues 133–145 followed by residues 175–400 of the L-protein of HBsAg relative to the open reading frame on a Hepatitis B virus of ad serotype (this polypeptide is referred to as L*; see EP 0 414 374). HBsAg within the scope of the invention may also include the preS1-preS2 -S polypeptide described in EP 0 198 474 (Endotronics) or analogues thereof such as those described in EP 0 304 578 (McCormick and Jones). HBsAg as herein described can also refer to mutants, for example the 'escape mutant' described in WO 91/14703 or European Patent Application Publication Number 0 511 855 A1, especially HBsAg wherein the amino acid substitution at position 145 is to arginine from glycine.

Normally the HBsAg will be in particle form. The particles may comprise for example S protein alone or may be composite particles, for example (L*.S) where L* is as defined above and S denotes the S-protein of HBsAg. The said particle is advantageously in the form in which it is expressed in yeast.

Herpes Simplex virus Glycoprotein D is located on the viral envelope, and is also found in the cytoplasm of infected cells (Eisenberg R. J. et al J. of Virol. 1980 35 428–435). It comprises 393 amino acids including a signal peptide and has a molecular weight of approximately 60 kD. Of all the HSV envelope glycoproteins this is probably the best characterized (Cohen et al J. Virology 60 157–166). In vivo it is known to play a central role in viral attachment to cell membranes. Moreover, glycoprotein D has been shown to be able to elict neutralizing antibodies in vivo (Eing et al, J. Med Virology 127: 59–65). However, latent HSV2 virus can still be reactivated and induce recurrence of the disease despite the presence of high neutralizing antibodies titre in the patients sera. It is therefore apparent that the ability to induce neutralizing antibody alone is insufficient to adequately control the disease.

The mature recombinant truncated glycoprotein D (rgD2t) or equivalent proteins secreted from mammalian cells, is preferably used in the vaccine formulations of the present invention. Equivalent proteins include glycoprotein gD from HSV-1.

In a preferred aspect the $rgD_2t$ is HSV-2 glycoprotein D of 308 amino acids which comprises amino acids 1 though 306 of the naturally occurring glycoprotein with the addition of Asparagine and Glutamine at the C terminal end of the truncated protein. This form of the protein includes the signal peptide which is cleaved to yield a mature 283 amino acid protein. The production of such a protein in Chinese Hamster ovary cells has been described in Genentech's European patent EP-B-139 417 and Science 222 p524, and Biotechnology p527 June 1984. Such a vaccine when formulated with small MPL according to the present invention has a superior therapeutic potential as compared to known $rgD_2t$ formulations.

Whilst certain experimental and commercially available vaccines afford excellent results it is an accepted fact that an optimal vaccine needs to stimulate not only neutralising antibody but also needs to stimulate as effectively as possible cellular immunity mediated through T-cells.

A particular advantage is that the vaccine formulations of the invention are very effective in inducing protective immunity, even with very low doses of antigen.

They provide excellent protection against primary and recurrent infection and stimulate advantageously both specific humoral (neutralising antibodies) and also effector cell mediated (DTH) immune responses.

To make 3 deacylated monophosphoryl lipid A with a small particle size, in general not exceeding 120 nm the procedure described in GB 2 220 211 may be followed to obtain known 3D-MPL, (or commercial MPL of larger particle size may be purchased from Ribi Immunochem.) and the product may then be sonicated until the suspension is clear. The size of the particles may be estimated using dynamic light scattering as described hereinbelow. In order to maintain the MPL size in the 100 nm range after being formulated with aluminium hydroxide, the antigen and the buffer, Tween 80 (polyoxyethylene (20) sorbitan monooleate) or sorbitol can be added. Under these conditions, it has been established that MPL does not aggregate in the presence of phosphate buffer, as may happen during formulation without them. By doing so, the final formulation is further defined and characterized. It has also been established that under these conditions, MPL still interacts with aluminium hydroxide and the antigen forming one single entity.

A clear solution of MPL forms an aspect of the invention. This solution may be sterilised by passing through a filter.

Preferably the size of the particles is in the range 60–120 nm.

Most advantageously the particle size is below 100 nm.

The MPL as defined above will normally be present in the range of 10–200 μg, preferably 25–50 μg per dose wherein the antigen will be typically present in a range of 2–50 μg per dose or more. The vaccine formulation of the present invention may additionally contain further immunostimulants, in a preferred embodiment the vaccines of the present invention may include QS21 (sometimes referred to as QA21). This is an HPLC fraction of a saponin extract derived from the bark of a tree, Quillaja Saponaria Molina and a method for its production is disclosed in U.S. Pat. No. 5,057,540.

The carrier may optionally be an oil in water emulsion, a lipid vehicle, or aluminium hydroxide (aluminium hydroxide salt).

Non-toxic oil in water emulsions preferably contain a non-toxic oil, e.g. squalene and an emulsifier such as Tween 80, in an aqueous carrier. The aqueous carrier may be, for example, phosphate buffered saline.

Preferably the vaccine formulations will contain an antigen or antigenic composition capable of eliciting an immune response against a human or animal pathogen, which antigen or antigenic composition is derived from HIV-1, (such as gp120 or gp160; see WO 92/06113 and references therein), herpes virus such as gD or derivatives thereof or Immediate Early protein such as ICP27 from HSV-1 or HSV-2, gB (or derivatives thereof) from Human cytomegalovirus, or gpI, II or III from Varicella Zoster Virus, or from a hepatitis virus such as hepatitis B virus or from other viral pathogens, such as Respiratory Syncytial virus, human papilloma virus or Influenza virus, or against bacterial pathogens such as Salmonella, Neisseria, Borrelia (for example OspA or OspB or derivatives thereof), or Chlamydia, or Bordetella for example P.69, PT and FHA, or against parasites such as plasmodium or Toxoplasma. The vaccine formulations of the present invention may contain a tumour antigen, and be useful as an anticancer vaccine.

One embodiment of the invention is HAV antigen (for example as in Havrix) in admixture with MPL and aluminium hydroxide as described hereinbelow.

A further embodiment of the invention is HB Virus Surface (HBsAg) antigen (for example as in Engerix-B) in admixture with MPL and aluminium hydroxide as described hereinbelow.

A further specific embodiment of the invention is HBsAg antigen as (L*,S) particles, defined hereinabove, in admixture with MPL and aluminium hydroxide.

Hepatitis A plus Hepatitis B combination vaccines may also be prepared in accordance with the invention.

A further embodiment is a formulation according to the invention comrising mature truncated glycoprotein D (rgD2t) or equivalent proteins as described hereinabove. Yet a further embodiment is a formulation of the invention comprising an OspA antigen or derivative thereof from *Borrelia burgdorferi*. For example, antigens, particularly OspA antigens from the ZS7 or B31 strains may be used. Yet a further embodiment is a formulation of the invention comprising a flu antigen. This provides an improved influenza vaccine, especially if a 'split' virus is used.

The formulation may also be useful for utilising with herpetic light particles such as described in International Patent Application No. PCT/GB92/00824 and, International Patent Application No. PCT/GB92/00179.

Advantagously the vaccine composition of the invention contains other antigens so that it is effective in the treatment or prophylaxis of one or more other bacterial, viral or fungal infections.

For example, hepatitis vaccine formulations according to the invention referably contain at least one other component selected from non-hepatitis antigens hich are known in the art to afford protection against one or more of the following: diphtheria, tetanus, pertussis, Haemophilus influenzae b (Hib), and polio.

Preferably the vaccine according to the invention includes HBsAg as hereinabove defined.

Particular combination vaccines within the scope of the invention include a DTP (diphtheria-tetanus-pertussis)-hepatitis B combination vaccine formulation, an Hib-Hepatitis B vaccine formulation, a DTP-Hib-Hepatitis B vaccine formulation and an IPV (inactivated polio vaccine)-DTP-Hib-Hepatitis B vaccine formulation.

The above combinations may advantageously include a component which is protective against Hepatitis A, especially the killed attenuated strain derived from the HM-175 strain as is present in Havrix.

Suitable components for use in such vaccines are already commercially available and details may be obtained from the World Health Organisation. For example the IPV component may be the Salk inactivated polio vaccine. The pertussis vaccine may comprise whole cell or acellular product.

Advantageously the hepatitis or combination vaccine according to the invention is a paediatric vaccine.

The invention in a further aspect provides a vaccine composition according to the invention for use in medical therapy, particularly for use in the treatment or prophylaxis of infections include viral and bacterial infections or for immuno therapeutic treatment of cancer. In a preferred aspect the vaccine according to the invention is a therapeutic vaccine useful for the treatment of ongoing infections, for example hepatitis B or herpetic infections in humans suffering therefrom.

Vaccine preparation is generally described in New Trends and Developments in Vaccines, edited by Voller et al, University Park Press, Baltimore, Md. U.S.A. 1978. Encapsulation within liposomes is described, for example, by Fullerton, U.S. Pat. No. 4,235,877. Conjugation of proteins to macromoloecules is disclosed, for example, by Likhite, U.S. Pat. No. 4,372,945 and by Armor et al, U.S. Pat. No. 4,474,757.

The amount of antigen in each vaccine dose is selected as an amount which induces an immunoprotective response without significant, adverse side effects in typical vaccinees. Such amount will vary depending on which specific immunogens are employed. Generally it is expected that each dose will comprise 1–1000 µg of total immunogen, preferably 2–100 µg, most preferably 4–40 µg. An optimal amount for a particular vaccine can be ascertained by standard studies involving observation of antibody titres and other responses in subjects. Following an initial vaccination, subjects may receive a boost in about 4 weeks.

In a further aspect of the present invention there is provided a method of manufacture of a vaccine effective in preventing or treating infection, wherein the method comprises mixing the antigen with a carrier and MPL wherein the particle size of the MPL is no greater than 120 nm, normally 60–120 nm, preferably about or less than 100 nm.

The following examples illustrate the invention and its advantages.

EXAMPLE 1

Preparation of MPL with a particle size of 60–120 nm

Water for injection is injected in vials containing lyophilised 3-de-O-acylated monophosphoryl lipid A (MPL) from Ribi Immunochem, Montana using a syringe to reach a concentration of 1 to 2 mg per ml. A preliminary suspension is obtained by mixing using a vortex. The content of the vials is then transferred into 25 ml Corex tubes with round bottoms (10 ml suspension per tube) and the suspension is sonicated using a water bath sonicator. When the suspension has become clear, the size of the particles is estimated using dynamic light scattering (Malvern Zetasizer 3). The treatment is continued until the size of the MPL particles is in the range 60–120 nm.

Suspensions can in some cases be stored at 4 degrees C. without significant aggregation up to 5 months. Isotonic NaCl (0.15M) or isotonic NaCl plus 10 mM phosphate induces a rapid aggregation (size >3–5 µm).

EXAMPLE 2

Production of large scale sterile soluble MPL with a particle size of below 100 nm Lyophilised 3 de-O-acylated monophosphoryl lipid A was obtained from Ribi Inmunochem, and suspended in water for injection (WFI). The suspension was continuously pumped through an ultrasound flow cell. The flow cell is typically made of glass or stainless steel with PTFE seals so as to comply with GMP constraints. The Ultrasound is generated utilising an Ultrasound generator and a titanium sonic horn (sonotrode) acquired from Undatim Ultrasonics (Louvain-La-Neuve, Belgium). A heat exchanger is incorporated into the loop to avoid degradation of the product by heat. The temperature of the MPL between the inlet and the outlet of the flow cell is kept between +4° C. and 30° C., and the difference of the temperature between the inlet and outlet is kept below 20° C. It will be appreciated that heat is also removed as the material passes through the apparatus.

BRIEF DESCRIPTION OF THE DRAWING

The apparatus used is schematically depicted in FIG. 1.

2.1. Sonication

The MPL powder (50 to 500 mg) is suspended in WFI at concentration between 1 and 2 mg/ml.

Figure 1:
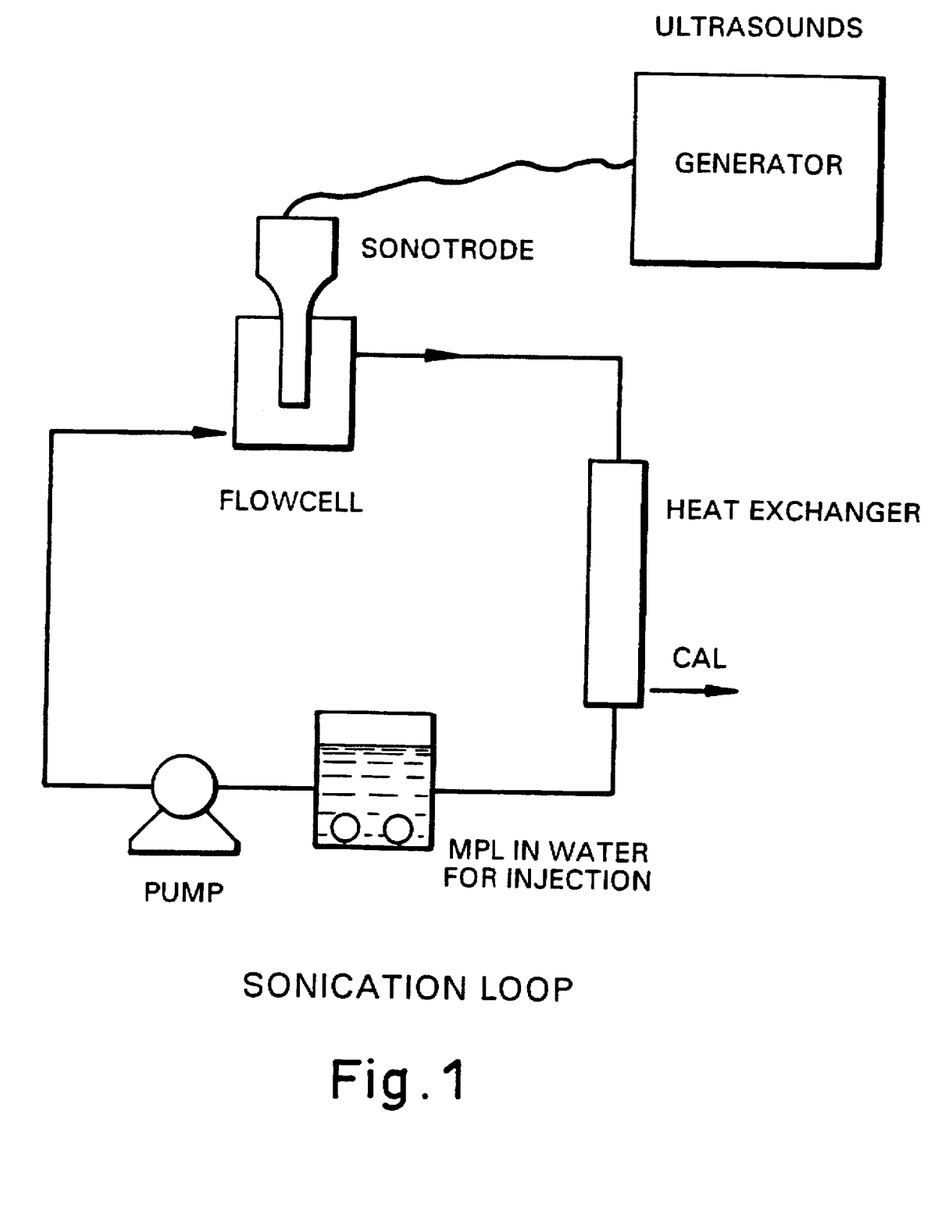

The MPL suspension (under stirring conditions) is continuously pumped through the sonication loop (see FIG. 1) at a flow rate between 50 and 100 ml per minute in order to reach the equilibrium temperature of the system which is between +4° and +15° C.

The own frequency spectrum of the sonic horn in the configuration of the system (Power, Flow Cell, Liquid Flow rate, T°.) is set according to suppliers instructions for the equipment. Pre-established limits are fixed between 19000 Hertz ahd 21000 Hertz for the 20,000 Hertz transducer.

The generator allows the control of the optimal efficiency of the sonication (more transmission of energy with less heat) at a given time interval.

The temperature during the process is maintained below 30° C. to avoid MPL degradation.

The process is complete when the particle size is reduced below 100 nm and the solution is clear by visual inspection. During the sonication process samples are taken for particle size evaluation by photocorrelation spectroscopy (dynamic light scattering) using a Malvern Zetasizer type 3 in the same manner as example 1. The total liquid residence time in the sonicator flow cell is calculated to be between 2.5 and 3.5 minutes (see table 1), using a 20 ml. capacity flow cell and 50 ml/min recirculation flow rate. This flow rate gives an average residence time of 25 seconds per cycle and normally less than 10 cycles are needed to obtain the desired-effect of small particle MPL.

2.2. Sterilization Process

The resulting "solubilized" MPL is sterilized by dead end filtration on a hydrophilic PVDF 0.22 mcm membrane. The observed pressure is usually below 1 bar. At least 25 mg of "solubilized" MPL are easily processed per square centimetre with a recovery above 85%.

2.3. Storage/Stability

Sterile "solubilized" MPL is stored at +2° to 8° C. Stability data (Malvern) did not show any significant difference of particle size after 6 months storage. (See Table 2).

EXAMPLE 3

Hepatitis B vaccine formulation

MPL (particle size less than 100 nm) was obtained as described in Example 1. Aluminium hydroxide was obtained from Superfos (Alhydrogel).

The MPL was resuspended in water for injection at a concentration varying from 0.2 to 1 mg/ml by sonication in a water bath until the particles reach a size of between 80 and 500 nm as measured by photo correlation light scattering.

1 to 20 µg of HBsAg (S-antigen as in Engerix B) in phosphate buffer solution at 1 mg/ml) is adsorbed on 30 to 100 µg of aluminium hydroxide (solution at 10.38 $Al^{3+}$ mg/ml) for one hour at room temperature under agitation. To the solution is then added 30 to 50 µg of MPL (solution 1 mg/ml). Volume and osmolarity are adjusted to 600 µl with water for injection and phosphate buffer 5x concentrated. Solution is incubated at room temperature for 1 hour and kept at 4° C. until use. Maturation of the formulation occurs during storage. This represents 10 injecting doses for testing in mice.

EXAMPLE 4

Hepatitis A vaccine formulation

MPL (particle size less than 100 nm) was obtained as described in Example 1. Aluminium hydroxide was obtained from Superfos (Alhydrogel).

HAV (360 to 22 EU per dose) is preadsorbed on 10% of the aluminium hydroxide final concentration (0.5 mg/ml). The MPL (12.5 to 100 µg per dose) is added to the solution.

The remaining aluminium hydroxide is added to the solution and left for one hour at room temperature. Volumes are adjusted with phosphate buffer (phosphate 10 mM, NaCl 150 mM) and the final formulation is then stored at 4° C. until use.

EXAMPLE 5

Comparison Of Adjuvant Efficacy Of A Recombinant Herpes Simplex Glycoprotein D Subunit Vaccine 5.1 In this study, the ability of various Al(OH)3 MPL formulations to improve the protective immunity of a truncated glycoprotein D from Herpes Simplex virus type 2 (HSV2) (rgD2t) was evaluated in the prophylactic and therapeutic guinea pig models. Immunogenicity studies were also performed in primates. The aim of these experiments was to investigate the impact of the size of 3-de-O-acylated monophosphoryl lipid A (MPL) particles on the immunogenicity and protective efficacy of rgD$_2$t Al(OH)3 MPL formulations in rodents and in primates. Three different Al(OH)3 MPL formulations of small size MPL were tested:
Al(OH)3 MPL 100 nm (as described previously)
Al(OH)3 MPL 100 nm with sorbitol
Al(OH)3 MPL 100 nm with Tween.

5.2 Antigen-adjuvant preparations and immunisation schedules 5.2.1. Antigen formulations Aluminium hydroxide (Al(OH)3) was obtained from Superfos (Alhydrogel Superfos, Denmark). MPL was obtained from Ribi Immunochem Research Inc.

5.2.1.1. rgD$_2$t (Al(OH)3)/MPL TEA

MPL was resuspended by sonication in a water bath, to give sizes comprising between 200 and 600 nm. The preparation was prepared according to patent application WO92/16231, and was stored at 4° C. until use.

A dose contained 5 µg rgD2t, 0.5 mg Al(OH)3 and 50 µg MPL.

5.2.1.2. rgD$_2$t/Al(OH)3/MPL 100 nm

MPL (particle size less than 100 nm) was obtained as described in Example 1. rgD$_2$t was adsorbed on aluminium hydroxide and incubated 1 h room temperature. MPL was added to the solution at the required concentration and incubated further for 1 hour at room temperature.

The preparation was completed with PBS to reach a final concentration of 10 mM PO4, 150 mM NaCl. The final formulation was further incubated for 30 minutes at room temperature and stored at 4° C. until use.

A dose contained 5 µg rgD$_2$t, 0.5 mg Al(OH)3 and 50 µg MPL.

5.2.1.3. rgD$_2$t/Al(OH)3/MPL 100 nm sorbitol

MPL was prepared as described in Example 1. rgD$_2$t was adsorbed on aluminium hydroxide and incubated 1 h at room temperature. A 50% sorbitol solution was then added to reach a final concentration of 5%. Tris 10 mM solution was then added to make up the final desired volume, and the solution was incubated 1 h at room temperature under agitation.

The formulation was stored at 4° C. until use.

A dose contained 5 µg rgD2t, 0.5 mg Al(OH)3 and 50 µg MPL.

5.2.1.4. rgD$_2$t/Al(OH)3/MPL 100 nm tween

MPL was prepared as described in Example 1. In order to maintain the MPL size to 100 nm, Tween 80 was added to the solution at a concentration such that it will be equal to 0.01% in the final formulation. The formulation is then prepared as described in formulation 5.2.1.3 above.

A dose contained 5 µg rgD2t, 0.5 mg Al(OH)3 and 50 µg MPL.

5.3. Guinea pig prophylactic experiment

In these experiments, groups of guinea pigs were vaccinated at days 0 and 28 with 5 µg rgD2t in two different aluminium hydroxide MPL formulations. Immunisations were given subcutaneously in an 0.5 ml dose. One month after the second vaccination, guinea pigs were challenged intravaginally with $10^5$ pfu of HSV2 strain MS. They were monitored daily for the development of primary and recurrent HSV2 disease (days 4 to 39 post challenge).

5.3.1. Guinea pig therapeutic experiments

In these experiments, guinea pigs were challenged at day 0 with $10^5$ pfu HSV2 strain MS. After recovery from primary infection, they were evaluated daily for recurrent herpetic disease (days 13 to 21). Guinea pigs were vaccinated at days 21 and 42 with rgD$_2$t Al(OH)3 MPL vaccine. Vaccines were administrated subcutaneously in a 0.5 ml dose. Animals were monitored daily for herpetic lesions until day ±60 or ±84.

5.3.2. Primate Immunogenicity studies

The immunogenicity of rgD$_2$t Al(OH)3 combined with MPL in sorbitol was evaluated in African Green Monkeys. Groups of monkeys were vaccinated at days 0 and 28 with 20 µg rgD2t and 0.5 mg Al(OH)3 combined with 50,20 or 5 µg MPL in sorbitol. Specific humoral (ELISA and neutralising titers) and effector cell mediated (delayed type hypersensitivity response:DTH) immune responses were evaluated. Each monkey group contained 5 animals. The formulations were administered intramuscularly in a 1 ml dose. Preparation of the formulations was done as described above. Animals were bled ± every two weeks for antibody determination.

DTH response was tested 14 days after the second vaccination. A description of the skin test is given below.

5.4. Read-outs

Assays were set up to evaluate the specific antibody response induced by vaccination with rgD2t Al(OH)3 MPL formulations (determination anti-rgD$_2$t ELISA titers and anti-HSV2 neutralising titers). The protective efficacy of these gD2 formulations was assessed in the prophylactic and therapeutical guinea pig models. Immunogenicity studies were also conducted in monkeys. Specific humoral and DTH responses were evaluated.

5.4.1. ELISA and neutralising titers

Anti-rgD$_2$t antibody titers and anti-HSV2 neutralising activity were determined according the methods described in patent application No. WO92/16231

5.4.2. Delayed type hypersensitivity (DTH)

The rgD$_2$t formulations were also tested for their ability to induce a T cell specific immune response in monkeys as measured by the induction of delayed-type hypersensitivity (DTH) responses.

African Green monkeys were vaccinated at days 0 and 28 with 20 µg gD2 vaccine formulation administered intramuscularly. They were skin tested 14 days after the second vaccination by intradermal injection on the belly of 15 or 5 µg of rgD$_2$t in saline. They were also skin tested with saline as control. The site of injection was inspected 24 and 48 hours later for erythema and induration and the size of these local reactions was measured.

5.4.3. Guinea pig intravaginal challenge model

The guinea pig model for HSV genital infection has been described by L. Stanberry et al (J. of Infectious Diseases 1982, 146: 397–403; Intervirology 1985, 24: 226–231). Briefly, in prophylactic experiments, the guinea pigs were challenged intravaginally with $10^5$ pfu of HSV2 strain MS, one month after the last vaccination. The clinical course of primary disease was monitored by daily observation of the incidence and severity of genital skin lesions during the 4–12 day post challenge period. Animals were then examined daily for evidence of recurrent herpetic lesions from days 13 to 39. In therapeutic experiments, guinea pigs were challenged at day 0 with $10^5$ pfu HSV2 strain MS. After recovery from primary infection, they were evaluated daily for recurrent herpetic disease (days 13 to 21) and were then randomized according to their primary and recurrent scores (providing an equivalent distribution of animals with mild to severe infection in each group) to receive either no treatment or vaccination. Vaccines were administered on days 20 and 41 after challenge. The pattern of recurrent disease was generally observed until ±70 post challenge.

The herpetic lesions were quantitated by using a lesion score scale ranging from 0 to 32.

| Lesion type | Score |
|---|---|
| None | 0 |
| Vaginal lesions | |
| Bleeding | 0.5 |
| Redness for one or two days without bleeding | 0.5 |
| Redness and bleeding for a day | 1 |
| Redness without bleeding for at least 3 days | 1 |
| External herpetic vesicles | |
| <4 small vesicles | 2 |
| ≧4 small vesicles or only one big vesicle | 4 |
| ≧4 large lesions | 8 |
| Fusing large lesions | 16 |
| Fusing large lesions on all external genital area | 32 |

Clinical read-outs

Primary infection

Lesion severity=sum of the daily scores for the days 4 to 12 post infection. The lesion severity is expressed as arithmetic mean ±SD as well as median (more appropriate for non-parametric test).

Primary infection incidences=% of animals having experienced a maximum lesion score of 0, 0.5, 1, 2, 4, 8 or 16 (rarely 32).

Primary infection index=Σi (max.score i)×(incidence %) with i=0, 0.5, 2, 4, 8 or 16.

Recurrent disease

Recurrence day number=number of recurrence days for the days 13 to 39 post-infection. One recurrence is preceded and followed by a day without lesion and characterized by at least two days with erythema or one day with vesicle(s). Recurrence day numbers are expressed as arithmetic means ±SD and medians.

Recurrence severity=sum of the daily scores for the days 13 to 39 post-infection. Results are expressed as arithmetic means ±SD and medians.

5.5. Results

The protective efficacy of different rgD$_2$t Al(OH)3 MPL formulations was compared in prophylactic and therapeutic experiments in guinea pigs. Immunogenicity studies were also conducted in primates. The aim of these experiments was to compare the immunogenicity and protective efficacy of rgD$_2$t Al(OH)3 combined with different MPL particles size.

5.5.1. Prophylactic experiments

Two experiments were performed to evaluate the potential of different rgD$_2$t Al(OH)3 MPL vaccines to provide protection against primary and recurrent HSV2 disease, when administered to guinea pigs prior to intravaginal viral inoculation.

EXPERIMENT 1

Comparison of MPL 100 nm sorbitol versus MPL TEA

Group of female hartley guinea pigs (200–250 g) were immunized at days 0 and 28 with 5 μg rg$D_2$t Al(OH)3 combined with small size MPL particles (100 nm; MPL in sorbitol), or with larger MPL particles (MPL in TEA). Control animals were injected according to the same protocol with adjuvant alone or were untreated. The animals were bled 14 and 28 days after the second vaccination for antibody determinations by ELISA and neutralization assays. They were challenged 29 days after the second vaccination with $10^5$ pfu of HSV2 strain MS intravaginally. After challenge, the guinea pigs were monitored daily for clinical signs of acute infection (days 4 to 12 post challenge) and for evidence of recurrent herpetic disease (days 13 to 39 post challenge).

a) Induction of humoral immunity

As shown in Table 3, higher ELISA and neutralizing titers were induced when the small size MPL particles were used in the rg$D_2$t Al(OH)3 formulation.

b) Effect of vaccination on primary HSV2 infection (Table 3)

As compared to the control group that became infected and experienced acute primary infection, both vaccinated groups showed significantly reduced lesion severity ($p<0.00005$). A significantly lower skin lesion incidence was observed in the rg$D_2$t Al(OH)3 MPL 100 nm vaccinated group ($p<0.06$).

c) Effect of vaccination on recurrent HSV2 disease

Results are given in Table 4. As compared to the controls, both vaccines were able to alter the development of recurrent herpetic disease, as measured by reduction in the number of recurrent episodes ($p<0.02$ for rgD$_2$t Al(OH)3 MPL 100 nm)

d) Conclusions

Both formulations were able to provide significant protection against primary infection and to reduce recurrent disease. These results show that the rgD$_2$t Al(OH)3 formulation containing small size MPL particles has a very potent prophylactic efficacy.

EXPERIMENT 2

Efficacy of Al(OH)3 MPL 100 nm

Hartley guinea pigs (200–250 g) were immunized at days 0 and 28 with 5 µg gD2 formulated in Al(OH)3 MPL 100 nm. Immunizations were given subcutaneously in a 0.5 ml dose. A dose of 50 µg MPL was used in the Al(OH)3 MPL formulation. Control animals were injected according the same protocol with adjuvant alone or were untreated. The animals were bled 14 and 28 days after the second vaccination for antibody determination by ELISA and neutralization assays. The guinea pigs were challenged 29 days after the last immunization with $10^5$ pfu of HSV2 strain MS intravaginally.

a) Induction of humoral immunity

As shown in Table 3, the vaccinated group produced good ELISA and neutralizing titers. Control group did not develop any detectable antibody response.

b) Effect of vaccination on primary HSV2 infection (Table 3)

As compared to the control group that became infected and experienced acute primary infection, the vaccinated group showed significant reduced lesion severity ($p<0.00005$) and incidence ($p<0.002$). There was no evidence of external skin lesions in any of the vaccinated guinea pigs.

c) Effect of vaccination on recurrent HSV2 disease (Table 4)

As compared to the controls, the rgD$_2$t Al(OH)3 MPL vaccine was able to alter the development of recurrent herpetic disease, as measured by significant reduction in the severity of recurrent episodes ($p<0.00005$), and in the incidence of recurrent episodes ($p<0.01$).

d) Conclusions rgD$_2$t Al(OH)3 combined with small size MPL particles is very potent in providing protection against primary and recurrent HSV2 infection in guinea pigs.

From the experiments described above one could conclude that small size MPL Al(OH)3 formulations obtained through two different strategies induce at least as potent prophylactic response as does large size MPL Al(OH)3 formulation. In addition small size MPL has the advantage of being sterilised easily before use.

5.5.2. Therapeutic experiments

The aim of these experiments was to compare the therapeutical potential of different rgD$_2$t Al(OH)3 MPL formulations on the course of the recurrent herpetic disease in guinea pigs with established HSV2 infection.

Guinea pigs were inoculated intravaginally at day 0 with $10^5$ pfu HSV2 strain MS. They were monitored daily for clinical signs of acute infection (days 4 to 12) as well as for evidence of recurrent herpetic disease (days 13 to 20). Animals were randomized into different experimental groups according to their primary and recurrent scores, providing an equivalent distribution of animals with mild to severe infection in each group. Guinea pigs without evidence of clinical signs of infection were not enrolled in the protocol. Vaccines were administrated subcutaneously at days 21 and 42 after challenge.

The therapeutic efficacy of rgD$_2$t Al(OH)3 MPL formulations was evaluated in three different experiments.

EXPERIMENT 1

Efficacy of rgD$_2$t Al(OH)3 combined with large size MPL particles (MPL in TEA)

Guinea pigs experiencing recurrent disease were randomized to receive either 20 µg rgD$_2$t Al(OH)3 combined with large size MPL particles (MPL TEA) or adjuvant alone. Vaccines were administered at days 21 and 42 post challenge. The pattern of recurrent disease was observed until day 84.

As shown in Table 3, the rgD$_2$t Al(OH)3 MPL TEA formulation was not effective in reducing the ongoing recurrent disease.

EXPERIMENT 2

Efficacy of rgD$_2$t Al(OH)3 MPL 100 nm

Two groups of guinea pigs were either vaccinated with 20 µg rgD$_2$t Al(OH)3 combined with small size MPL particles (MPL 100 nm) or untreated.

Vaccinations were given at days 20 and 41 post challenge. The recurrent disease was followed until day 69.

As shown in Table 5 in contrast with data in Experiment 1 where large size MPL was used, vaccination with the rgD$_2$t Al(OH)3 MPL 100 nm vaccine altered the recurrences of established HSV2 disease, as compared to the control group, by significantly decreasing the recurrence severity (−39%, $p<0.05$) and the recurrence day number (−28%, $p<0.1$).

EXPERIMENT 3

Comparative efficacy of Al(OH)3 combined with small size MPL particles

In this experiment, a third strategy for obtaining small size MPL was used: addition of tween, eg Tween 80.

The experimental groups were as follows:

Group 1 (n=15): 20 µg rgD$_2$t/Al(OH)3 MPL 100 nm with tween

Group 2 (n=15): 20 µg rgD$_2$t/Al(OH)3 MPL 100 nm with sorbitol

Group 3 (n=16): controls

Controls were either untreated or vaccinated with Al(OH)3 MPL alone. Vaccines were administered at days 21 and 42 post challenge. The pattern of recurrent disease was observed until day 60 post challenge.

The results are shown in Table 5. A clear significant therapeutical effect was observed in animals vaccinated with the two rgD$_2$t/Al(OH)3 MPL formulations. Both formulations significantly reduced the recurrence severity, the recurrence day number and the number of recurrent episodes.

Conclusions

A very potent therapeutic effect against established recurrent HSV2 genital disease was observed with rgD$_2$t Al(OH)3 MPL formulations containing small size MPL particles (ca. 100 nm). In contrast, this therapeutic effect was not observed when large MPL size particles (MPL in TEA) were added to the rgD$_2$t Al(OH)3 vaccine.

In conclusion, results obtained in guinea pigs clearly demonstrate the prophylactic efficacy of rgD$_2$t Al(OH)3 MPL formulations prepared with small size MPL particles. These formulations have an improved therapeutic potential as compared to rgD$_2$t Al(OH)3 combined with large size MPL particles.

5.5.3 Immunogenicity studies of rgD$_2$t Al(OH)3 combined with small size MPL particles in primates The immunogenicity of rgD$_2$t Al(OH)3 combined with small size MPL articles (MPL 100 nm sorbitol) was evaluated in primates (African Green Monkeys). Doses of 50, 20 or 5 µg of MPL 100 nm were combined with 20 µg of rgD₂t and Al(OH)3 (0.5 mg). Two vaccinations were given at 0 and 1 months. Specific humoral (ELISA and neutralizing titers) and effector cell mediated (DTH) immune responses were measured.

a) Experimental procedure

Three groups of 5 African Green Monkeys were vaccinated at days 0 and 28 with 20 µg of gD2t Aluminium hydroxide formulation containing 50, 20 or 5 µg of MPL. Immunisations were given intramuscularly in a 1 ml dose. Animals were bled every two weeks for antibody determination by ELISA (anti-gD2 titers) and neutralization assays. The three vaccine formulations were also compared for their ability to induce a T cell mediated immunity in vivo, as measured by the induction of a specific delayed-type hypersensitivity (DTH) response. Three monkeys in each group were skin tested 14 days after the second vaccination with 15 or 5 µg of gD2t, given in saline on the belly. They were also skin tested with saline alone as control. Erythema and induration at the site of the intradermal inoculation were monitored 24 hours and 48 hours later.

b) Results

Serological and DTH responses are shown in Table 6. Groups of monkeys vaccinated with the gD₂t Al(OH)3 formulation containing either 50 or 20 µg of MPL produced significantly more neutralizing antibodies than the group receiving the 5 µg MPL dose (p<0.003 and p<0.008, respectively). There was no significant difference in the ELISA or neutralizing titers measured in the 50 or 20 µg MPL groups. A correlation between the MPL dose and the effect on the effector cell mediated immune response was observed. A strong DTH response was detected in the majority of the monkeys (¾) vaccinated with the 50 or 20 µg MPL formulation. In contrast, only one monkey from the 5 µg MPL group developed a skin test response.

c) Conclusions

The data described above demonstrate that the adjuvant effect of Al(OH)3 combined with small size MPL particles is also effective in primates and is not restricted to small animal species. A correlation between the MPL dose and the immunogenicity of the rgD₂t Aluminium hydroxide MPL formulation could be observed in monkeys, with 20 and 50 µg giving the best serological and DTH responses.

EXAMPLE 6

CLINICAL STUDIES with Lyme and Hepatitis B vaccines and small MPL 6.1. Lyme disease vaccine comprising a fusion protein of NS1(1–81) from influenza virus and OspA derived from *B. burgdorferi* ZS7.

Preparations of formulations 6.1.1. NS1-OspA/aluminium hydroxide

NS1-OspA prepared according to the procedures described in WO 93/04175 was adsorbed on aluminium hydroxide and incubated 1 hr at room temperature. Final volume was adjusted with phosphate buffer (PO4 10 mM, NaCl 150 mM). Formulation was stored at 4° C. until use.

A dose contains 10 µg NS1-OspA/500 µg aluminium hydroxide 6.1.2. NS1-OspA/aluminium hydroxide/MPL NS1-OspA was adsorbed on aluminium hydroxide and incubated 1 hr at room temperature. MPL prepared as described previously was then added to the formulation and incubated again 1 hr at room temperature. The formulation was then adjusted to the final volume with phosphate buffer (10 mM PO4, 150 mM NaCl). Formulation was stored at 4° C. until use.

A dose contains 10 µg OspA/500 µg Al(OH)3/50 µg MPL 6.1.3. Immunization schedule Human volunteers were injected three times intramuscularly with 1 ml of a given formulation at days 0, 31 and 62. Sera were taken 30 days post I, II and III.

They were then analysed by ELISA for total IgG anti OspA and for LA-2 like antibody response in an inhibition test (LA-2 Mab was shown to be protective antibody against infection in mice).

6.2. HBsAg/MPL formulations in humans 6.2.1. Preparation of Formulations

HBsAg 20 µg/Aluminium hydroxide 500 µg

HBsAg was adsorbed on the total final amount of aluminium hydroxide and final volume was adjusted with phosphate buffer saline (PO4 10 mM, NaCl 150 mM) at 1 ml per dose. Formulation wa stored at 4° C. until use.

6.2.2. HBsAg 20 µg/Aluminium hydroxide 100 µg

HBsAg was formulated as described previously but adsorbed only on 100 µg of Al(OH)3. The final volume was (1 ml) dose 6.2.3. HBsAg 20 µg/Aluminium hydroxide 100 µg/MPL 50 µg HBsAg was adsorbed on 100 µg aluminium hydroxide and incubated 1 h at room temperature. MPL was then added at the acquired concentration and incubated 1 h at room temperature. The formulation was then adjusted to the final volume (1 ml per dose) with appropriate buffer (as above) and stored at 4° C. until use.

6.2.4. Immunization schedule

Human volunteers (20 per group) were injected I.M. with 1 ml of one of the given formulations. Sera were collected on months 0, 1, 3 and 6. They were analysed for neutralizing antibodies with the commercially available Abbot test.

6.3. RESULTS

Table 8 shows that MPL used in combination with aluminium hydroxide and NS1-OspA in a form of particles of 100 nm is efficient at producing higher-antibody titers of inhibitory nature than the antigen on aluminium hydroxide and that the kinetics of seroconversion are faster.

This established that for a soluble antigen, like NS1-OspA, in humans, MPL formulated as small particle keeps the adjuvant properties that it already exhibited in animals with other soluble antigens.

Table 7 shows that the adjuvant effect lost by reducing the amount of aluminium hydroxide formulation present in Hepatitis B formulations can be recovered by adding MPL in the form described in this patent. The MPL also improves the seroconversion rate.

EXAMPLE 7

Combination vaccine formulation–Hepatitis B +Hepatitis A

HBsAg is adsorbed on 90% of the final amount of aluminium hydroxide (0.5 mg/ml) and incubated overnight at room temperature. The pH is adjusted to 6.2 and the preparation is left 14 days at room temperature for maturation.

Hepatitis A antigen at 360 to 22EU per dose, in the form of an inactivated derivative of the HM-175 strain (as in Havrix) is preadsorbed on 10% of the aluminium hydroxide final concentration (0.5 mg/ml). The remaining aluminium hydroxide is then added to the solution and left for one hour at room temperature under agitation.

The HAV adsorbed on aluminium hydroxide is then added to the HBsAg formulation.

MPL (particle size less than 100 nm) is added to the HAV/HBsAg solution at a final concentration of 12.5 to 100 µg per 1 ml dose, the volume is adjusted to the final dose volume, and the formulation is stored at 4° C. until used.

EXAMPLE 8

Combination vaccines containing additional antigens

Combination vaccines may be prepared by adding one or more of the desired antigens to the formulations described in Example 2 or Example 3 or Example 4 above.

EXAMPLE 9

Increase Of Humoral Immunity And Induction Of Cell Mediated Immunity By Immunization Of Mice With HBsAg formulated With Aluminium Hydroxide And MPL 9.1. Effect Of Al(OH)3 + Mpl On Induction Of Anti-HBs Antibodies Balb/c mice were immunized by the subcutaneous route or by the intradermal route with recombinant HBsAg adsorbed on Al(OH)3 with MPL as adjuvant. Mice were immunized twice with HBsAg/Al/MPL formulations and the antibody response was measured after the first and the second doses. Total Ig were measure by ELISA or AUSAB kit (Abbott Lab, Ill.) and a particular attention was given to the induction of antibodies of the IgG2a isotype since this isotype is mainly induced by secretion of g-Interferon. The induction of this isotype thus indirectly reflects the activation of cell mediated immunity, namely the activation of Th1.

The ratio HBsAg/MPL has been investigated as well as the size of MPL particles.

9.1.1. EXPERIMENT I—Effect of MPL (>500 nm) dose on immunogenicity of rec.HBsAg adsorbed on Al(OH)3

Groups of 10 female Balb/c mice were injected by the subcutaneous route with 2.5 mcg of recHBsAg adsorbed on 50 mcg of Al+++ (as Al(OH)3) and increasing amounts of MPL (3.1 to 50 mcg) with a particle size of >500 nm. The mice were injected twice in a volume of 100 mcl and at 2 weeks interval. They were bled 2 weeks after the first injection (partial bleeding) and one week after the booster. Total anti-HBs IgG and specific IgG2a were measured by ELISA using recHBsAg as capture antigen. The titers were expressed as the reciprocal of the dilution corresponding to 50% of the maximal value (mid-point dilution). The results indicate an increase of both specific IgG and IgG2a with increasing doses of MPL, particularly for doses of 12.5 to 50 mcg. The effect is seen for both primary and secondary responses and is particularly obvious for IgG2a (up to 20 fold increase) indirectly indicating a secretion of g-interferon induced by the immunization with MPL.

9.1.2. EXPERIMENT II—Comparison of clinical lots of adsorbed recHBsAg containing or not containing MPL (>500 nm)

3 clinical lots of recHBsAg adsorbed on Al(OH)3 were prepared:lot DSAH16 contained no MPL and served as control. Lots DSAR501 and 502 were prepared in a similar way (20 mcg of recHBsAg adsorbed on 0.5 mg Al+++ as Al(OH)3) but contained 50 mcg of MPL (>500 nm).

The 3 lots were injected subcutaneously to groups of 10 mice (200 mcl containing 2.5 mcg HBsAg, 100 mcg Al+++ and 6.25 mcg MPL), twice at 2 weeks interval. The mice were bled at day 14 and 1 week after the booster. Anti-HBs antibodies were measured using AUSAB kit or an in-house ELISA for either IgG or IgG2a. The results are given in table 2. They indicate that, 2 weeks after the first injection, the 2 lots containing MPL induce a very significant anti-HBs response (12.4 and 41.9 mIU/ml) while the lot which does not contain MPL only induces a marginal response (0.75 mIU/ml). The number of responders is also higher with MPL (9/10 and 9/10 versus 1/10 in absence of MPL). The effect of MPL is confirmed after the booster since the titers obtained for lots DSAR501 and 502 are about 6 fold higher than that observed without MPL.

This indicates that, at least in mice, MPL (>500 nm) can improve both the kinetics of the anti-HBs response and the level of the anti-HBs response.

These results were confirmed when specific IgG and IgG2a are measured after immunization with lots DSAH16 (without MPL) and DSAR502 (with MPL): the anti-HBs IgG titer is 5 (primary response) and 3 (secondary response) times higher when MPL is present.

For the IgG2a response, the effect of MPL is even more striking, at least after the second dose, indicating a preferential induction of IgG2a. This indirectly reflects activation of cell-mediated immunity (secretion of gamma-interferon) by the preparation containing MPL.

9.1.3. Experiment III: Effect of MPL (<100 nm) dose on immunogenicity of recombinant HBsAg adsorbed on Al(OH)3

Groups of 10 mice (Balb/c, female, 7 weeks old) were injected subcutaneously with 1 mcg of recombinant HBsAg adsorbed on 50 mcg of Al+++ (as Al(OH)3) and in presence of increasing amounts (3.1 to 25 mcg) of MPL(<100 nm). The mice were injected twice at 2 weeks interval with a volume of 200 mcl. They were bled 2 weeks after the first injection and 1 week after the booster. The anti-HBs response was evaluated by ELISA (total Ig, IgG, IgG2a) on pooled sera. The titers were expressed as mid-point dilutions (reciprocal of the dilution giving 50% of the highest values). The results indicate that as few as 3.1 mcg of MPL induce a strong increase of the antibody response both for primary and secondary responses. The response culminates for 6.25 mcg and decreases afterwards to become similar to that found without MPL when high doses of MPL (25 mcg) are used. The pattern of the antibody response is similar for IgG, IgG2a and total Ig. It contrasts with results obtained for MPL of higher size (>500 nm) and shows that small size (<100 nm) particles of MPL are more effective than larger size (>500 nm) particles (at least for humoral immunity), since less MPL is needed to obtain the maximal effect. The highest activity of small size MPL was confirmed in several experiments.

As shown for larger size MPL (>500 nm), the adjuvant effect of MPL is higher for IgG2a than for total IgG or Ig. At the maximal effect of the secondary response (6.25 mcg of MPL), there is a 25 fold increase for IgG2a while the increase for IgG or total Ig was 7.6 and 4.3 respectively.

9.2. Induction of Cell-Mediated Immunity by recHBsAg adsorbed on Al(OH)3—effect of MPL If humoral immunity is sufficient to protect against Hepatitis B, the induction of cell-mediated immunity (CTL, Th1) could be of particular importance for the treatment of the disease.

New formulations are required however for therapeutic vaccines since Al(OH)3 is capable of improving humoral immunity but not cell mediated immunity.

We have investigated the effect of MPL on the induction of Th1 cells capable of secreting IL-2 and g-(i.e. gamma) interferon in Balb/c mice immunized with recHBsAg adsorbed on Al(OH)3.

9.2.1. EXPERIMENT I—Effect of MPL (>500 nm) on induction of Th1 cells after immunization of Balb/c mice with Al(OH)3 adsorbed HBsAg A group of 10 Balb/c mice (female, 5 weeks old) were immunized by injection in each footpad of 30 mcl containing 10 mcg of HBsAg, 15 mcg of Al+++ (as Al(OH)3) and 15 mcg of MPL. Control mice were injected similarly with the same amount of recHBsAg either mixed with FCA (positive control) or adsorbed on Al(OH)3 without MPL (negative control).

Six days after the immunization, the mice were killed and the popliteal lymph nodes were removed. The lymph node cells (LNC 2.105/ml) were cultivated for different periods of time (24 hrs to 74 hrs) in RPMI medium supplemented with 1% of negative mouse serum and containing 5 mcg/ml of recHBsAg. After termination of the culture, the amount of L-2, INF-g and IL-4 secreted in the medium was measured. IL-2 was estimated by its ability to stimulate the proliferation (evaluated by incorporation of 3H-Thymidine) of an IL-2-dependent CTL line (VDA2 cells) and the titer was expressed as stimulation index (SI=amount of 3H-Thymidine incorporated in stimulated cells/amount of 3H-Thymidine incorporated in non stimulated cells). The amount of IL-4 and INF-g was measured using commercial ELISA kits (Holland Biotechnology for IFN-g and Endogen for IL-4). The titers were expressed in pg of IFN-g/ml.

The results indicate that no significant amount of IL-2, IL-4 or INF-g is secreted by LNC from mice immunized with HBsAg adsorbed on Al(OH)3. On the contrary, high levels of IL-2 (I.S.=38 at 48 hrs) and a significant amount of INF-g are secreted by LNC from mice immunized with HBsAg adsorbed on Al(OH)3+MPL. This secretion is similar (INF-g) or higher (IL-2) to that observed for mice immunized with HBsAg+FCA and the in vitro secretion occurs earlier.

No IL-4 was detected after immunization with HBsAg adsorbed on Al(OH)3 even in presence of MPL.

This secretion profile indicates that specific Th1 cells (IL-2, INF-g) have been induced by immunization with adsorbed HBsAg in presence of MPL but not in absence of MPL. However, no Th2 (IL-4) were detected in these conditions of immunization.

9.2.2. EXPERIMENT II—Effect of the dose of MPL (<100 nm) on the induction of Th1 cells after immunization of Balb/c mice with Al(OH)3 adsorbed recHBsAg Groups of 5 Balb/c mice were immunized in each of the 2 footpads with 30 mcl containing 10 mcg of recHBsAg adsorbed on 15 mcg of Al+++ (as Al(OH)3) and with increasing amounts of MPL (100 nm, 0 to 15 mcg).

Six days after the injection, the mice were killed and the popliteal lymph node cells (LNC) were cultivated at 2.106 cells/ml in RPMI supplemented with 1% negative mouse serum for different periods of time (24 hrs to 96/25) in presence of 5 mcg/ml of recHBsAg.

The secretion of IL-2 was measured by stimulation of the proliferation of VDA2 cells and concentration of IL-2 is expressed as Stimulation Index (SI); the secretion of INF-g was measured using a commercial kit and expressed in pg/ml.

It was found that the secretion of IL-2 is dramatically increased by the lower dose of MPL (7.5 mcg) and a maximal effect is obtained for 15 mcg of MPL.

The secretion of IL-2 is generally more important at 24 hrs than at 48 or 72 hrs.

The secretion of INF-g is absent when HBsAg is adsorbed on Al(OH)3 in absence of MPL. A small dose (7.5 mcg) of MPL induces a secretion of INF-g and again, the maximal effect is obtained for 15 mcg of MPL. Contrary to what is observed for IL-2, the secretion of INF-g is delayed in the culture and increases with time up to 96 hours.

Taken together these data indicate that MPL (less than 100 nm) is a potent inducer of Th1 when combined with HBsAg adsorbed on Al(OH)3. The effect of a formulation containing HBsAg adsorbed on Al(OH)3 and MPL on the induction of both humoral and cell-mediate immunity in Balb/c mice has been investigated. The results indicate that MPL clearly improves the kinetics of the anti-HBs response since much more anti-HBs antibodies are found after both the primary and secondary immunizations. The quality of the anti-HBs is also modified and a preferential induction of IgG2a has been observed, reflecting indirectly secretion of INF-g and thus induction of a cell-mediated immunity.

Direct evaluation of the induction of Th1 cells by formulations containing HBsAg, Al(OH)3 and MPL clearly indicates that MPL is a potent inducer of Th1 cells secreting both IL-2 and INF-g. This kind of formulation is thus important in the development of therapeutic vaccines.

Best results were obtained using MPL of less than 100 nm particle size.

For Tables showing the results of experiments described above, see Tables 9–14 below.

13. Conclusions

Overall the data suggests that small MPL is an improved immunostimulant in primates including man, over large size MPL. This combined with the ability to make large scale sterile lots renders small MPL as a suitable immunostimulant for a range of human or animal health vaccines.

TABLE 1

MPL particle and filtration recovery using different sonication parameters

| Trial n° | Concentration (mg/ml) | Total residence time in the flow cell (min) | Particle size before filtration (nm) | Recovery after filtration (%) |
|---|---|---|---|---|
| 16 | 1 | 2,5 | 92 | 104 |
| 17 | 1 | 3 | 79 | 78,5 |
| 18 | 1 | 3,5 | 95 | 86,4 |
| 19 | 2 | 2,8 | 77 | N.A. |
| 20 | 1 | 2,8 | 98 | N.A. |

TABLE 2

Particle size stability of a sterile MPL solution by photon correlation spectroscopy (Malvern) at 1 mg/ml

| Trial n° | Particle size filtration (nm) | Particle size after stability at 4° C. (nm) | | | |
|---|---|---|---|---|---|
| | | 8 days | 1 month | 3 months | 6 months |
| 9 | 94 | 81 | 74 | 88 | 82 |

TABLE 3

PROPHYLACTIC EFFICACY OF rgD$_2$t Al(OH)3 MPL FORMULATIONS IN GUINEA PIGS
HUMORAL RESPONSE AND EFFECT TO VACCINATION ON PRIMARY HSV2 DISEASE

| | | Ab TITERS (GMT) | | PRIMARY INFECTION | | | | | | | | |
|---|---|---|---|---|---|---|---|---|---|---|---|---|
| | | 28 D POST III | | LESION SEVERITY* | | LESION SCORE INCIDENCES** % | | | | | | PI |
| GROUP | FORMULATION | ELISA | NEUTRA | Arith. mean +/− SD | Median | 0 | 0.5 | 1 | 2 | 4 | 8 | 16 | index*** |
| | Experiment 1 | | | | | | | | | | | |
| 1n = 12 | rgD$_2$t 5 µg Al(OH)3/MPL (sorbitol) | 10439 | 673 | 2.2 ± 3.1 | 0.5 | 50 | 17 | 0 | 33 | 0 | 0 | 0 | 75 |
| 2n = 12 | rgD$_2$t 5 µg/Al(OH)3/MPL TEA | 5454 | 378 | 4.6 ± 6.3 | 1.5 | 42 | 8 | 8 | 25 | 17 | 0 | 0 | 130 |
| 3n = 11 | controls | <100 | <50 | 55.3 ± 51.8 | 55 | 18 | 0 | 0 | 0 | 27 | 0 | 55 | 988 |
| | Experiment 2 | | | | | | | | | | | |
| 1n = 10 | rgD$_2$t/Al(OH)3 MPL 100 nm | 21039 | 696 | 0.5 ± 0.7 | 0 | 60 | 30 | 10 | 0 | 0 | 0 | 0 | 25 |
| 2n = 10 | controls | <100 | <50 | 28.5 ± 29.1 | 31.5 | 30 | 0 | 0 | 0 | 10 | 40 | 20 | 680 |

*Sum of the lesion scores for the days 4 to 12 post-infection
**Lesion scores: no lesion (0), vaginal lesions (0.5 or 1), external skin vesicles (2, 4, 8 or 16)
***Primary infection index = Σi (Max.score i) × (incidence %); with i = 0, 0.5, 1, 2, 4, 8 or 16

TABLE 4

PROPHYLACTIC EFFICACY OF rgD$_2$t Al(OH)3 MPL FORMULATIONS IN GUINEA PIGS
EFFECT TO VACCINATION ON RECURRENT HSV2 DISEASE

| | | RECURRENT DISEASE | | | | | | | | | |
|---|---|---|---|---|---|---|---|---|---|---|---|
| | | REC. SEVERITY* | | REC. DAY NUMBER** | | REC. EPISODE NUMBER INCIDENCE (%) | | | | | |
| GROUP | FORMULATION | Arith. mean +/− SD | Median | Arith. mean +/− SD | Median | 0 | 1 | 2 | 3 | 4 | 5 |
| | Experiment 1 | | | | | | | | | | |
| 1n = 12 | rgD$_2$t 5 mg/Al(OH)3 MPL 100 nm (sorb.) | 5.4 ± 6.2 | 3.5 | 4 ± 5 | 2.5 | 33 | 42 | 8 | 8 | 8 | 0 |
| 2n = 12 | rgD$_2$t 5 µg/Al(OH)3/MPL TEA | 6.5 ± 5.9 | 6.5 | 4.3 ± 3.9 | 3 | 27 | 27 | 9 | 27 | 9 | 0 |
| 3n = 11 | controls | 8 ± 5.4 | 9 | 5.1 ± 3.1 | 6 | 18 | 0 | 18 | 64 | 0 | 0 |
| | Experiment 2 | | | | | | | | | | |
| 1n = 10 | rgD$_2$t Al(OH)3/MPL 100 nm | 1.6 ± 3.9 | 0 | 0.5 ± 1.1 | 0 | 80 | 20 | 0 | 0 | 0 | 0 |
| 2n = 10 | controls | 6.1 ± 6 | 6.75 | 4.3 ± 4.3 | 4.5 | 40 | 0 | 20 | 20 | 0 | 20 |

*Sum of the lesion scores for the days 13 to 39 post-infection
**Number of recurrence days for the days 13 to 39 post-infection
One recurrence is preceded and followed by a day without lesion and characterized by at least two days with erythema or one day with vesicle(s)
'Sorb' in Experiment 1 means Sorbitol

TABLE 5

THERAPEUTIC EFFICACY OF rgD$_2$t Al(OH)3 MPL FORMULATIONS:

| | | THERAPEUTIC EFFECT | | | |
|---|---|---|---|---|---|
| | | SEVERITY* | | REC. DAY NUMBER** | |
| GROUP | FORMULATION | Arith. mean +/− SD | Median (% versus conts) | Arith. mean +/− SD | Median (% versus conts) |
| | Experiment 1 | | | | |
| 1n = 18 | rgD$_2$6 20 µg/Al(OH)3/MPL TEA | ND | ND | ND | 11 |
| 2n = 18 | controls | ND | ND | ND | |
| | Experiment 2 | | | | |
| 1n = 14 | rgD$_2$t 20 µg/Al(OH)3 MPL 100 nm | 11.1 ± 8.7(−39%)p < 0.05 | 10.25(−41%)p < 0.1 | 8.4 ± 6(−28%)p < 0.1 | 8.5(−23%)p < 0.31 |
| 2n = 13 | controls | 18.3 ± 10.3 | 17.5 | 11.7 ± 6.8 | 11 |
| | Experiment 3 | | | | |
| 1n = 15 | rgD$_2$t 20 µg/Al(OH)3/MPL 100 nm; tween | 10.3 ± 10.1 | 6(−54%)p < 0.07 | 6.3 ± 5.8 | 4(−43%)p < 0.1 |
| 2n = 15 | rgD$_2$t 20 µg/Al(OH)3 MPL 100 nm; sorb. | 8.3 ± 6.7 | 6.5(−50%)p < 0.03 | 5.5 ± 4.4 | 4(−43%)p < 0.1 |
| 3n = 16 | controls | 12.5 ± 8.1 | 13 | 8.5 ± 4.5 | 7 |

TABLE 5-continued

THERAPEUTIC EFFICACY OF rgD₂t Al(OH)3 MPL FORMULATIONS:

| | THERAPEUTIC EFFECT REC. EPISODE NO.*** | |
|---|---|---|
| GROUP | Arith. mean +/− SD | Median (% versus conts) |
| 1n = 18 | ND | 7 |
| 2n = 18 | ND | 5 |
| 1n = 14 | 3.3 ± 2 | 4 |
| 2n = 13 | 4.4 ± 2.1 | 4 |
| 1n = 15 | 2.7 ± 2 p < 0.1 | 3(−25%)p < 0.1 |
| 2n = 15 | 2.7 ± 1.5 | 3(−25%)p < 0.1 |
| 3n = 16 | 3.6 ± 1.6 | 4 |

*Sum of the lesion scores for the days 21 to 60 post-infection
**Total days animals experienced recurrent lesions for the days 21 to 60 post-infection
***Recurrence episode number for the 21 to 60 post-infection. One episode is preceded and followed by a day without lesion and characterized by at least two days with erythema (score = 0.5) or one day with external vesicle(s) (score >= 2) Immunotherapeutical treatment: Subcutaneous injections at days 21 and 42 post-infection. Statistical analysis: Wilcoxon rank sum test versus adjuvant controls (not significant for p > 0.1:NS). Sorb. means sorbitol.

TABLE 6

IMMUNOGENICITY OF gD2t ALUMINIUM HYDROXIDE
MPL 100 nm (sorbitol)
IN PRIMATES
SEROLOGICAL AND DTH RESULTS

| VACCINE | MONKEY No. | ANTIBODY RESPONSE* | | DTH RESPONSE** (Induration) | | |
|---|---|---|---|---|---|---|
| | | ELISA TITER | NEUTRA TITER | PBS | gD2 5 μg | gD2 15 μg |
| 20 μg gD2t | KQ 100 | 18630 | 800 | − | + | ++ |
| Aluminium | KQ 101 | 5554 | 1600 | − | − | − |
| hydroxide | KQ 102 | 14870 | 800 | − | ++ | +++ |
| 50 μg MPL | KQ 103 | 5486 | 1600 | − | ++ | +++ |
| | KQ 104 | 16270 | 1600 | ND | ND | ND |
| | GMT | 10655 | 1213 | | | |
| 20 μg gD2 | KQ 105 | 16170 | 800 | − | + | ++ |
| Aluminium | KQ 106 | 4389 | 800 | − | − | − |
| hydroxide | KQ 107 | 20440 | 1600 | − | ++ | +++ |
| 20 μg MPL | KQ 108 | 5613 | 800 | − | + | + |
| | KQ 109 | 6765 | 1600 | ND | ND | ND |
| | GMT | 8876 | 1056 | | | |
| 20 μg gD2t | KQ 110 | 2486 | 200 | − | − | − |
| Aluminium | KQ 111 | 9918 | 800 | − | ++ | +++ |
| hydroxide | KQ 112 | 2526 | 400 | − | − | − |
| 5 μg MPL | KQ 113 | 7137 | 400 | − | − | − |
| | KQ 114 | 8396 | 400 | ND | ND | ND |
| | GMT | 5181 | 400 | | | |

*Measured 14 days post II/GMT = geometric mean titer
ELISA titer = midpoint titer
NEUTRA titer = reciprocal of the highest serum dilution giving 100% protection against the cytopathogen effect
**skin test on day 14 post II
Induration 24 hrs reading
+ = 1 mm
++ = 1–5 mm
+++ = >5 mm

TABLE 7

| timing | N | Sero conversion | % | GMT | min. titer | max. titer |
|---|---|---|---|---|---|---|
| aluminium hydroxide (500 µg) HBsAg | | | | | | |
| pre | 20 | 0 | 0 | 0 | 0 | 0 |
| PI(month 1) | 20 | 10 | 50 | 6 | 1 | 58 |
| PII(month 3) | 20 | 19 | 95 | 80 | 7 | 565 |
| aluminium hydroxide (100 µg) HBsAg | | | | | | |
| pre | 20 | 0 | 0 | 0 | 0 | 0 |
| PI(month 1) | 19 | 7 | 36.8 | 4 | 1 | 56 |
| PII(month 3) | 19 | 18 | 94.7 | 24 | 2 | 320 |
| aluminium hydroxide (100 µg) HBsAg MPL | | | | | | |
| pre | 20 | 0 | 0 | 0 | 0 | 0 |
| PI(month 1) | 20 | 12 | 60 | 10 | 1 | 66 |
| PII(month 3) | 20 | 20 | 100 | 73 | 6 | 605 |

TABLE 8

Immunogenicity of clinical batches of OspA In Humans
Anti-OspA in the LA-2 inhibition assay
(ng equiv LA-2/ml) (GMT)

| Vaccine | Pre Do | Post I 30 D28 | Post II 30 D56 | Post III 30 D84 |
|---|---|---|---|---|
| NS1-OspA on Aluminium hydroxide | 118 | 233 | 409 | 768 |
| SC (%) | 2.6 | 77.2 | 86.5 | 100 |
| NS1-OspA + MPL on Aluminium hydroxide | 134 | 269 | 865 | 2424 |
| SC (%) | 2.6 | 88.6 | 97.2 | 100 |

N = 80
10 µg/dose
Im route

TABLE 9

EFFECT OF INCREASING DOSES OF MPL (>500 nm)
ON IMMUNOGENICITY OF recHBsAG ADSORBED ON AL(OH)₃

| | Anti-HBs Response | | | |
|---|---|---|---|---|
| | Total IgG | | IgG2a | |
| Amount of MPL (mcg/dose) | Days 14 | Day 21 | Day 14 | Day 21 |
| 0* | 69 | 743 | 3.2 | 11 |
| 3.13 | 122 | 541 | 3.8 | 20 |
| 6.25 | 296 | 882 | 6.4 | 24 |
| 12.5 | 371 | 1359 | 10 | 48 |
| 25 | 456 | 1493 | 18 | 138 |
| 50 | 403 | 1776 | 33 | 242 |

*HBsAg on Al.

TABLE 10

COMPARISON OF 3 CLINICAL LOTS WITH AND WITHOUT MPL
AUSAB RESPONSE

| Lot | Dose of HBsAg on Al(OH)₃(mcg) | Dose of MPL (mcg) | GMT Anti-HBs (mIU/ml) | |
|---|---|---|---|---|
| DSAH16 | 2.5 | 0 | 0.75 | 15.1 |
| DSAR501 | 2.5 | 6.25 | 12.4 | 96.7 |
| DSAR502 | 2.5 | 6.25 | 41.9 | 89.2 |

TABLE 11

COMPARISON OF 2 CLINICAL LOTS WITH AND WITHOUT MPL
(>500 nm) ANTI-HBs IGG AND IGG2A RESPONSE

| | Dose of HBsAg on Al(OH)₃(mcg) | Dose of MPL (mcg) | Anti-HBs Response | | | |
|---|---|---|---|---|---|---|
| | | | IgG | | IgG2a | |
| Lot | | | d15 | d21 | d15 | d21 |
| DSAH16 | 2.5 | 0 | 20 | 178 | <5 | 5 |
| DSAR502 | 2.5 | 6.25 | 113 | 641 | <5 | 28 |

TABLE 12

EFFECT OF MPL (<100 NM) DOSE ON IMMUNOGENICITY OF
REC HBsAG ADSORBED ON AL(OH)₃

| Dose of HBsAg adsorbed on Al(OH)₃ (mcg) | Dose on MPL (<100 nm) (mcg) | Anti-HBs Response | | | | | |
|---|---|---|---|---|---|---|---|
| | | Total 1G | | IgG | | IgG2a | |
| | | d15 | d21 | d15 | d21 | d15 | d21 |
| 1 | 0 | 30 | 637 | 67 | 516 | 15 | 99 |
| 1 | 3.12 | 312 | 2302 | 335 | 3532 | 167 | 1752 |
| 1 | 6.25 | 538 | 2719 | 856 | 3932 | 261 | 2521 |
| 1 | 12.5 | 396 | 2104 | 485 | 3625 | 125 | 1393 |
| 1 | 25.0 | 38 | 446 | 141 | 638 | 28 | 233 |

TABLE 13

EFFECT OF MPL (>500 nm) ON THE INDUCTION OF HBsAG SPECIFIC TH1 CELLS IN BALB/C MICE

| Dose of HBsAg | | In vitro secretion of | | | | | | | | |
|---|---|---|---|---|---|---|---|---|---|---|
| | | IL-2(SI) | | | INF-γ(pg/ml) | | | IL-4(pg/ml) | | |
| (mcg/mouse) | Formulation | 24 h | 48 h | 72 h | 24 h | 48 h | 72 h | 24 h | 48 h | 72 h |
| 20 | FCA | 1.3 | 2.0 | 8.0 | <125 | <125 | 385 | NT | NT | NT |
| — | FCA | 0.7 | 1.8 | 0.7 | <125 | <125 | <125 | NT | NT | NT |
| 20 | Al(OH)₃ | 1.0 | 1.4 | 1.2 | <125 | <125 | <125 | <40 | <40 | <40 |
| 20 | Al(OH)₃ + MPL (30 mcg) | 2 | 38 | 10 | <125 | 280 | 280 | <40 | <40 | <40 |

After immunization as described in the text, lump node cells were cultured with 5 mcg recHBsAg/ml for the indicated periods of time and the secretion of IL-2, INF-γ and IL-4 were measured using respectively VDA₂ T-cell line and 2 commercial ELISA kits.

TABLE 14

EFFECT OF DIFFERENT DOSES OF MPL(<100 NM) ON THE INDUCTION OF HBsAG SPECIFIC TH1 CELLS

| Dose of HBsAg | Dose of | In vitro secretion of | | | | | | |
|---|---|---|---|---|---|---|---|---|
| | | IL-2(SI) | | | INF-γ(pg/ml) | | | |
| (mcg/mouse) | MPL | 24 h | 48 h | 72 h | 24 h | 48 h | 72 h | 96 h |
| 20 | 0 | 2.6 | 28 | 21.8 | <67 | <67 | <67 | <67 |
| 20 | 7.5 | 207 | 173 | 58 | <67 | 207 | 522 | 698 |
| 20 | 15 | 270 | 71 | 36 | 275 | 878 | 1249 | 1582 |
| 20 | 30 | 41 | 59 | 36 | <67 | <67 | <67 | 207 |

We claim:

1. A sterile vaccine composition comprising an antigen, 3-O-deacylated monophosphoryl lipid A (3D-MPL) particles, and a suitable carrier, wherein the particles of 3D-MPL are small enough to give a clear aqueous suspension of 3D-MPL.

2. A vaccine composition as claimed in claim 1 in which the particle size of the MPL is in the range 60–120 nm.

3. A vaccine composition as claimed in claim 1 in which the particle size of the MPL is less than 100 nm.

4. A vaccine composition as claimed in claim 1 in which the carrier is aluminium hydroxide.

5. A vaccine composition as claimed in claim 1 in which the carrier is an oil in water emulsion or other lipid based vehicle.

6. A vaccine composition as claim in claim 1 in which comprises a viral antigen.

7. A vaccine composition as claimed in claim 6 wherein the antigen comprises a Hepatitis A antigen.

8. A vaccine composition as claimed in claim 7 wherein the Hepatitis A antigen is derived from the HM-175 strain.

9. A vaccine composition as claimed in claim 1 wherein the antigen comprises a hepatitis B antigen.

10. A vaccine composition as claimed in claim 9 wherein the antigen comprises Hepatitis B surface antigen (HBsAg) or a variant thereof.

11. A vaccine composition according to claim 9 additionally comprising a Hepatitis A antigen.

12. A vaccine composition as claimed in claim 1 wherein the antigen is HBsAg and comprises the S antigen of HBsAg.

13. A vaccine composition as claimed in claim 1 wherein the antigen is a surface antigen from Hepatitis B virus and comprises a pre-S sequence and the S antigen.

14. A vaccine composition as claimed in claim 1 wherein the antigen comprises a composite particle which contains a modified L protein of hepatitis B virus having an amino acid sequence comprising residues 12–52 followed by residues 133–145 followed by residues 175–400 of the L protein and the S-protein of HBsAg.

15. A vaccine composition as claimed in claim 1 comprising one or more hepatitis antigens and at least one other component selected from a non-hepatitis antigen which affords protection against one or more of the following: diphtheria, tetanus, pertussis, Haemophilus influenzae b (Hib), and polio.

16. A vaccine composition according to claim 1 comprising antigens selected from a DTP (diphtheria-tetanus-pertussis) HBsAg combination, an Hib-HBsAg combination, a DTP-Hib-HBsAg combination and an IPV (inactivated polio vaccine)-DTP-Hib-HBsAg combination.

17. A vaccine composition according to claim 16 additionally comprising a hepatitis A antigen.

18. A vaccine composition as claimed in claim 1 comprising an HSV glycoprotein D or an immunological fragment thereof.

19. A vaccine composition as claimed in claim 18 wherein the glycoprotein D is a truncated protein.

20. A vaccine composition as claimed in claim 1 wherein the antigen comprises HSVgD2 antigen and is devoid of the C terminal anchor region.

21. A vaccine composition as claimed in claim 1 wherein the 3-O-deacylated monophosphoryl lipid A is present in the range 10 μg–100 μg per dose.

22. A vaccine composition as claimed in claim 1 additionally comprising either polyoxyethylene (20) sorbitan mono-oleate or sorbitol.

23. A method of treating a human subject suffering from or susceptible to infection comprising administering an effective amount of a vaccine of claim 1.

24. A vaccine composition as claimed in claim 1 wherein the antigen is a soluble NS1-OspA fusion protein, where NS1 is influenza NS1 and OspA is Borrelia burgdorferi OspA.

25. The vaccine composition as claimed in claim 24 wherein the fusion protein is adsorbed on aluminum hydroxide.

26. 3-O-deacylated monophosphoryl lipid A of a particle size less than 120 nm.

27. A clear sterile aqueous suspension of 3-O-deacylated monophosphoryl lipid A (3D-MPL) particles.

28. The suspension of 3-O-deacylated monophosphoryl lipid A (3D-MPL) particles of claim 27 which has been filter-sterilized.

29. The sterile suspension of 3D-MPL particles of claim 28 filter-sterilized through a 220 nm hydrophilic membrane.

30. The sterile suspension of 3D-MPL particles of claim 28 which is stable when stored at 2° to 8° C.

31. A method for preparing a clear aqueous suspension of 3-O-deacylated monophosphoryl lipid A particles comprising suspending the 3-O-deacylated monophosphoryl lipid A (3D-MPL) particles in water and reducing the size of the 3D-MPL particles in the resulting suspension until the suspension is clear.

32. The method of claim 31 which further comprises filter-sterilizing the clear suspension through a hydrophilic 220 nm membrane, thereby obtaining a clear aqueous sterile suspension of 3D-MPL particles.

33. The method of claim wherein 31 wherein the reduction of the size of the 3-D MPL particles is by sonication.

34. The clear aqueous suspension which is the product obtained by the method of claim 31.

35. A method for preparing a vaccine comprising admixing a clear aqueous sterile suspension of 3-O-deacylated monophosphoryl lipid A particles with an antigen.

36. The method of claim 35 wherein the antigen is adsorbed on aluminum hydroxide.

37. In a method for the manufacture of an antigen containing a medicament for the prophylaxis or treatment of infection, the improvement which comprises admixing said antigen with 3-O-deacylated monophosphoryl lipid A having a particle size which does not exceed 120 nm.

38. A vaccine formulation which comprises the interaction product of sterile 3-O-deacylated monophosphoryl lipid A 3D-MPL particles, aluminum hydroxide, and an antigen.

39. The vaccine formulation of claim 38 in which the MPL particles have been filter-sterilized through a 220 nm hydrophilic membrane.

40. The vaccine formulation of claim 39 in which the antigen is Hepatitis A antigen.

41. The vaccine formulation of claim 39 in which the antigen is Hepatitis B antigen.

42. An adjuvant composition comprising an aqueous stable suspension of 3-O-deacylated monophosphoryl lipid A (3D-MPL) particles, the particle size of the 3D-MPL being small enough to be filterable through a 220 nm hydrophilic membrane.

43. A sterile adjuvant composition comprising a filtered aqueous stable suspension of 3-O-deacylated monophosphoryl lipid A (3D-MPL) particles, the filtration recovery of the particles through a 220 nm hydrophilic membrane being at least 78.5%.

44. The adjuvant composition of claim 43 which includes an antigen.

45. The adjuvant composition of claim 44 wherein the antigen is adsorbed on aluminum hydroxide.

46. A sterile adjuvant composition comprising an aqueous stable suspension consisting essentially of 3-O-deacylated monophosphoryl lipid A (3D-MPL) particles filtered through a 220 nm hydrophilic membrane.

47. The adjuvant composition of claim 46 which includes an antigen.

48. The adjuvant composition of claim 47 wherein the antigen is adsorbed on aluminum hydroxide.

49. A sterile vaccine composition comprising an antigen, 3-O-deacylated monophosphoryl lipid A (3D-MPL) particles, and a suitable carrier, the particles of 3D-MPL being the recovery of filtration through a 220 nm hydrophilic membrane.

50. The sterile vaccine composition of claim 49 wherein the carrier is aluminum hydroxide.

51. A sterile vaccine composition comprising an antigen, a pharmaceutically acceptable carrier and 3-O-deacylated monophosphoryl lipid A (3D-MPL) consisting essentially of particles of less than 100 nm size.

52. The sterile vaccine composition of claim 51 wherein the carrier is aluminum hydroxide.

53. The sterile vaccine composition of claim 52 wherein the antigen is HBsAg.

* * * * *